(12) United States Patent
Rasco

(10) Patent No.: US 8,114,103 B2
(45) Date of Patent: Feb. 14, 2012

(54) SCALPEL BLADE PROTECTOR

(76) Inventor: James Edwin Rasco, The Woodlands, TX (US)

( * ) Notice: Subject to any disclaimer, the term of this patent is extended or adjusted under 35 U.S.C. 154(b) by 963 days.

(21) Appl. No.: 11/226,753

(22) Filed: Sep. 14, 2005

(65) Prior Publication Data

US 2007/0060934 A1   Mar. 15, 2007

(51) Int. Cl.
*A61B 17/32* (2006.01)

(52) U.S. Cl. .......................... 606/167; 30/151

(58) Field of Classification Search .............. 606/167; 30/2, 63, 151, 162, 335, 143, 156, 164, 236, 30/260, 284, 285, 286, 329, 163
See application file for complete search history.

(56) References Cited

U.S. PATENT DOCUMENTS

| | | | |
|---|---|---|---|
| 825,976 A * | 7/1906 | Neiglick .................... 30/162 |
| 895,511 A | 8/1908 | Sturgis |
| 3,906,626 A * | 9/1975 | Riuli ...................... 30/162 |
| 3,945,117 A | 3/1976 | Beaver |
| 4,414,974 A | 11/1983 | Dotson |
| 4,523,379 A * | 6/1985 | Osterhout et al. ............ 30/151 |
| 4,576,164 A | 3/1986 | Richeson |
| 4,735,202 A | 4/1988 | Williams |
| 4,844,070 A * | 7/1989 | Dee ....................... 606/167 |
| 5,071,426 A | 12/1991 | Dolgin et al. |
| 5,250,063 A | 10/1993 | Abidin et al. |
| 5,254,128 A | 10/1993 | Mesa |
| 5,275,606 A | 1/1994 | Abidin et al. |
| 5,292,329 A | 3/1994 | Werner |
| 5,299,357 A | 4/1994 | Wonderley et al. |
| 5,309,641 A | 5/1994 | Wonderly |
| 5,330,492 A * | 7/1994 | Haugen ........................ 606/167 |
| 5,342,379 A | 8/1994 | Volinsky |
| 5,366,468 A * | 11/1994 | Fucci et al. .................... 606/180 |
| 5,411,512 A | 5/1995 | Abidin et al. |
| 5,417,704 A | 5/1995 | Wonderly |
| 5,423,843 A | 6/1995 | Werner |
| 5,478,348 A | 12/1995 | Bajada |
| 5,569,281 A * | 10/1996 | Abidin et al. ................ 606/167 |
| 5,571,127 A * | 11/1996 | DeCampli .................... 606/167 |
| 5,599,351 A | 2/1997 | Haber et al. |
| 5,620,454 A | 4/1997 | Pierce |
| 5,662,669 A * | 9/1997 | Abidin et al. ................. 606/167 |
| 5,665,099 A | 9/1997 | Pilo et al. |
| 5,676,677 A | 10/1997 | Landis et al. |
| 5,752,968 A | 5/1998 | Jolly et al. |
| 5,792,162 A * | 8/1998 | Jolly et al. .................... 606/167 |
| 5,843,107 A | 12/1998 | Landis et al. |
| 5,868,771 A | 2/1999 | Herbert |
| 5,938,676 A * | 8/1999 | Cohn et al. ................... 606/167 |
| 5,941,892 A | 8/1999 | Cohn et al. |
| 6,070,326 A * | 6/2000 | Berns ............................. 30/2 |
| 6,293,020 B1 * | 9/2001 | Julien .......................... 30/350 |
| 6,464,701 B1 * | 10/2002 | Hooven et al. ................ 606/50 |
| 6,569,175 B1 | 5/2003 | Robinson |
| 6,626,925 B2 | 9/2003 | Newman |
| D504,513 S | 4/2005 | Morawski et al. |

(Continued)

*Primary Examiner* — Ryan Severson
*Assistant Examiner* — Jonathan W Miles
(74) *Attorney, Agent, or Firm* — Wong, Cabello, Lutsch, Rutherford, and Brucculeri LLP

(57) ABSTRACT

A scalpel blade protector comprises an inner housing attached to a scalpel handle, an outer housing and a blade guard slidably mounted between the inner and outer housings for movement between positions exposing and shielding the scalpel blade. The blade protector is attached to conventional scalpel handles. A first embodiment shows a blade protector for a flat scalpel handle. A second embodiment shows a blade protector for a round or hexagonal scalpel handle.

10 Claims, 2 Drawing Sheets

U.S. PATENT DOCUMENTS

| | | |
|---|---|---|
| 6,884,240 B1 | 4/2005 | Dykes |
| 7,022,128 B2 | 4/2006 | Morawski et al. |
| 7,087,067 B2 | 8/2006 | Kehr et al. |
| 7,153,317 B2 * | 12/2006 | Kanodia et al. ............... 606/167 |
| 7,156,231 B1 | 1/2007 | Austria |
| 7,159,713 B1 | 1/2007 | Austria |
| 7,172,611 B2 | 2/2007 | Harding et al. |
| 7,207,999 B2 | 4/2007 | Griffin et al. |
| 7,314,471 B2 | 1/2008 | Holman |
| 7,346,989 B2 | 3/2008 | Shi |
| 7,398,880 B2 | 7/2008 | Henry |
| 2002/0143352 A1 * | 10/2002 | Newman et al. ............... 606/167 |
| 2004/0087989 A1 | 5/2004 | Brenneman |
| 2004/0243161 A1 | 12/2004 | Kanadia et al. |
| 2005/0015104 A1 * | 1/2005 | Morawski et al. ............ 606/167 |
| 2005/0119680 A1 | 6/2005 | Dykes |
| 2005/0203555 A1 * | 9/2005 | Griffin et al. ................. 606/167 |
| 2006/0212058 A1 | 9/2006 | Djordjevic et al. |
| 2007/0255298 A1 | 11/2007 | Djordjevic et al. |

* cited by examiner

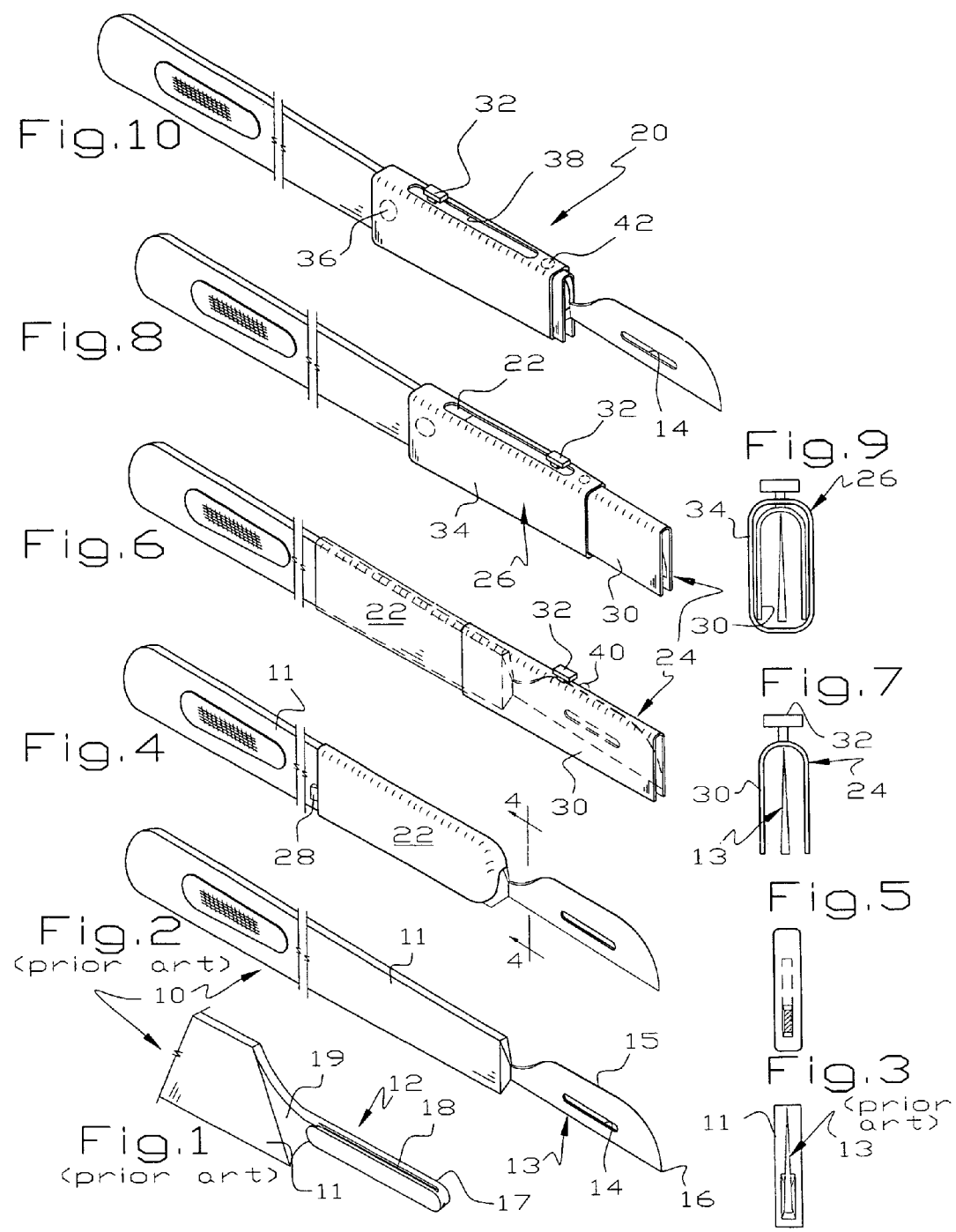

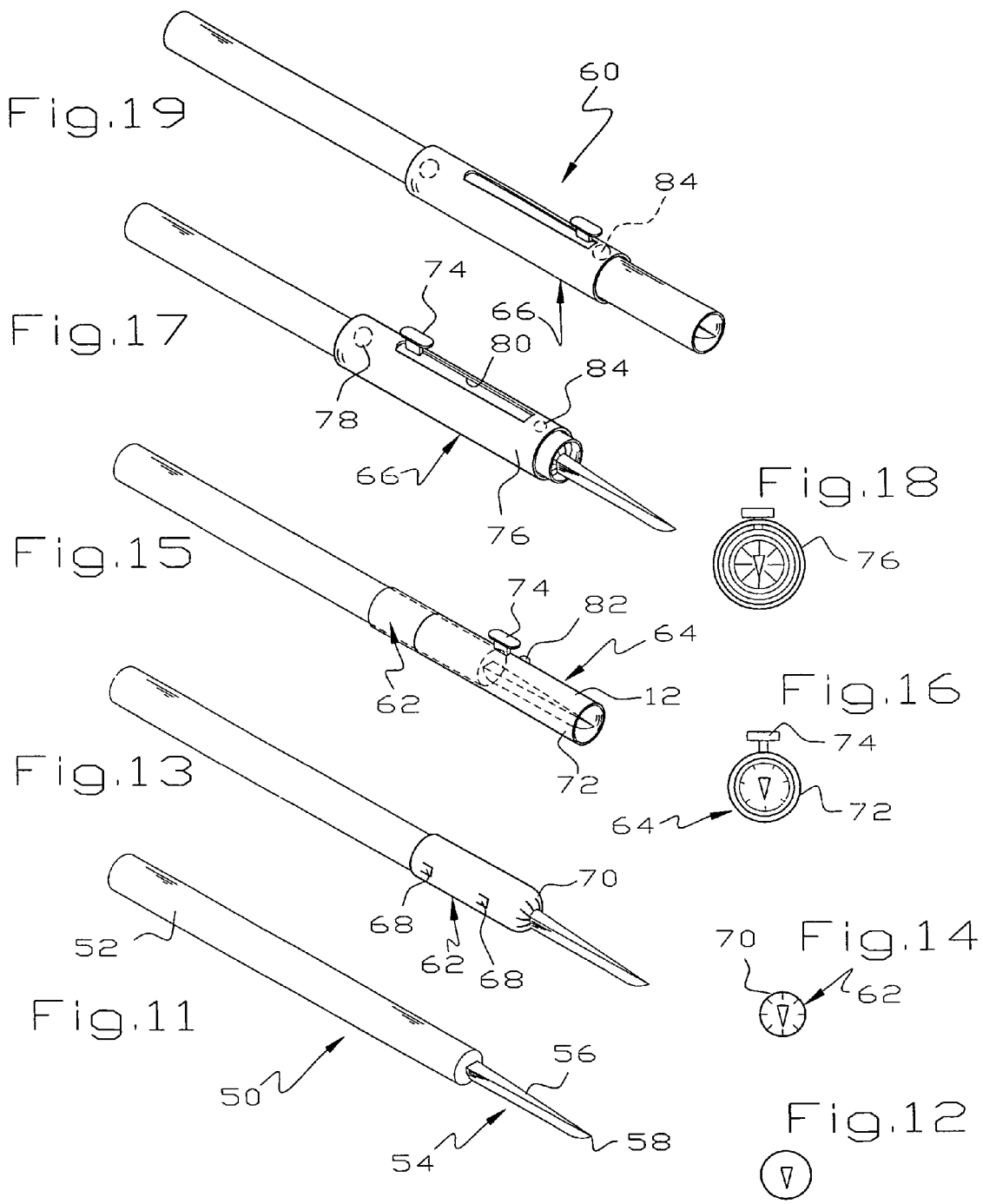

SCALPEL BLADE PROTECTOR

This invention relates to a blade protector for a surgeon's scalpel and more particularly to a blade protector for a conventional scalpel.

BACKGROUND OF THE INVENTION

A movement exists to encourage or require surgeon's scalpels to have blade protectors in an attempt to minimize accidental cuts during surgery. The broad concept is to provide a shield or guard that can be moved by the surgeon from a stowed position exposing the blade to an operative position covering the blade. Not surprisingly, there have been proposed a series of specially designed scalpels that incorporate blade protectors such as found in U.S. Pat. Nos. 3,906,626; 4,414,974; 4,576,164; 4,735,202; 5,292,329; 5,309,641; 5,330,492; 5,417,704; 5,423,843; 5,620,454; 5,868,771 and 6,626,925 as well as printed patent application 2004/0087989.

SUMMARY OF THE INVENTION

In this invention, it is recognized that many surgeons have become accustomed to conventional scalpel handles and are somewhat uncomfortable with handles that are specifically modified to provide movable blade guards. Accordingly, the scalpel guard of this invention is designed to fit onto conventional scalpel handles. Because most conventional scalpel handles are either flat or round/hexagonal, two different embodiments of this invention are illustrated.

In both embodiments, an inner housing is fixed to the scalpel handle in a suitable manner, such as with a friction fit, a removable adhesive, shrink fit or the like. In the event the inner housing is slightly loose on the scalpel handle, a wedge or other suitable member may be used to secure the inner housing to the handle. A blade guard is mounted on the inner housing for movement between an operative extended position shielding the scalpel blade and a stowed or retracted position exposing the blade. The blade guard includes a shoulder or protuberance so the surgeon can readily push or pull the blade guard to a desired position. An outer housing covers the blade guard and is attached in any suitable manner to the inner housing so the blade guard may readily slide between the inner and outer housings.

It is an object of this invention to provide an improved scalpel blade protector.

A further object of this invention is to provide an improved scalpel blade protector that may be positioned on a conventional scalpel without modifying the scalpel.

A more specific object of this invention is to provide a scalpel blade protector including an inner housing affixed to the scalpel handle, a blade guard movable between positions exposing and shielding the blade and an outer housing covering much of the inner housing and blade guard.

These and other objects and advantages of this invention will become more apparent as this description proceeds, reference being made to the accompanying drawings and appended claims.

BRIEF DESCRIPTION OF THE DRAWINGS

FIG. 1 is a partial isometric view of a conventional scalpel handle showing the blade attachment end;

FIG. 2 is an isometric view, similar to FIG. 1, showing the scalpel handle with a blade having the cutting edge up;

FIG. 3 is an end view of the scalpel of FIGS. 1 and 2;

FIGS. 4 and 5 are isometric and cross-sectional views of the scalpel of FIGS. 2 and 3 to which has been added an inner housing;

FIGS. 6 and 7 are isometric and end views of the scalpel and inner housing of FIGS. 4 and 5 to which has been added a slidable blade guard;

FIGS. 8 and 9 are isometric and end views of the scalpel, inner housing and blade guard of FIGS. 6 and 7 to which has been added an outer housing, illustrating the outer housing in an extended or shielding position over the scalpel blade;

FIG. 10 is an isometric view similar to FIG. 8 showing the blade guard in a retracted position exposing the scalpel blade;

FIG. 11 is an isometric view of another embodiment of a conventional scalpel showing the scalpel with the cutting edge down;

FIG. 12 is an end view of the scalpel of FIG. 11;

FIGS. 13 and 14 are isometric and end views of the scalpel of FIGS. 11 and 12 to which has been added an inner housing;

FIGS. 15 and 16 are isometric and end views of the scalpel and inner housing of FIGS. 13 and 14 to which has been added a slidable blade guard;

FIGS. 17 and 18 are isometric and end views of the scalpel, inner housing and blade guard of FIGS. 15 and 16 to which has been added an outer housing, illustrating the outer housing in an retracted position exposing the scalpel blade; and FIG. 19 is an isometric view similar to FIG. 17 showing the blade guard in an extended or shielding position covering the scalpel blade.

DETAILED DESCRIPTION

Referring to FIGS. 1-10, there is illustrated a conventional scalpel 10 having a flat handle 11 having an end 12 sculpted to receive a blade 13 having a slot 14 therein, a cutting edge 15 and a cutting tip 16. The end 12 provides an elongate rib 17 providing a notch 18 extending lengthwise and an inclined abutment 19. The rib 17, notch 18 and abutment 19 are sized and shaped to receive the slot 14 of the blade 13 and, in cooperation with the remainder of the blade 13, thereby attach the blade 13 to the handle 11. Provided on the scalpel 10 is a blade protector 20 comprising an inner housing 22, a blade guard 24 and an outer housing 26. As will become more fully apparent hereinafter, an important advantage of this invention is the ability to replace the blade 13 without removing the blade protector 20. Although FIGS. 2-9 appear to show the protected scalpel in the process of being assembled, this is for illustrative purposes only. The blade protector 20 is a unit and is attached in one motion.

The inner housing 22 is attached to the handle 11 in any suitable manner, such as by a friction fit. To this end, the inner housing 22 may be slightly elastic allowing it to be slipped over the end of the handle 11, after removing the blade 13. In the event the inner housing 22 does not snugly fit the scalpel handle 11, a wedge 28 or other suitable member may be inserted between the handle 11 and inner housing 22, as shown in FIG. 4. The inner housing 22 may be made of any suitable material, such as a medically approved polymer, and is mainly open so the blade 13 may be secured to the handle 11 after the blade protector 20 is in place.

In the alternative, the inner housing 22 may be secured to the handle 11 by the use of releasable adhesives, by a shrink fit or the like. In the event a shrink fit is selected, the material of the inner housing 22 is selected to shrink in response to the application of heat, as with a hair dryer or the like. After use, and before sterilizing the handle 11, the blade protector 20 may be removed simply by cutting the material of the inner housing 22.

The blade guard 24 slides on the outside of the inner housing 22 between a position exposing the blade 13 and a position shielding the blade 13, as may be seen by a comparison of FIGS. 8 and 10. The blade guard 24 is made of any suitable material, such as a medically approved polymer, and preferably includes a U-shaped guard 30 having an opening adjacent the non-cutting edge of the blade 13 and an operator 32 conveniently placed for the surgeon to push or pull in order to slide the blade guard 24 between its positions. It will, of course, be evident that the blade guard 24 may be closed and the operator 32 placed on the top of the handle 11 rather than on the bottom as shown.

The outer housing 26 is made of any suitable material, such as a medically approved polymer, and includes a closed generally rectangular member 34 secured to the inner housing 22 in a suitable manner, as by pressure welding in a spot or depression 36 rearwardly of the blade guard 34. The member 34 provides a slot 38 along its edge so the operator 32 is exposed through the outer housing 26. It will accordingly be seen that rearward movement of the blade guard 24 is limited by the physical connection between the inner and outer housings 22, 26.

The position of the blade guard 24 relative to the inner and outer housings 22, 26 may be controlled in any suitable manner. Because the blade guard 24 slides between the inner and outer housings, the position control may be friction between the blade guard 24 and the housings 22, 26. In other words, the blade guard 24 slides, but not readily, between the housings 22, 26. In the alternative, suitable locking means, such as a detent or bulge 40 on the blade guard 24 and one or more depressions 42 facing the detent 40. The detent 40 and depression 42, or other similar arrangement, may also provide a limit of outward movement of the blade guard 24 so it cannot accidentally be advanced off the handle 11.

Use of the scalpel 10 and blade protector 20 should now be apparent. The blade protector 20 slips over the end of the scalpel handle 11 and the blade 13 is then installed. To position the blade guard 24 in the shielding position around the blade 13, the operator 32 is advanced to a position covering the tip 16 of the blade 13, as shown in FIG. 8. To use the scalpel 10, the surgeon manipulates the operator 32 to retract the blade guard 24 thereby exposing the cutting edge 15 and tip 16 of the blade 13 as shown in FIG. 10. It will also be seen that the blade 13 may be removed from the handle 11 with the blade protector 20 in place. This is of significant advantage because surgeons periodically replace blades during surgery and are accustomed to continue using the same handle.

Referring to FIGS. 11-19, there is illustrated another embodiment of a conventional scalpel 50 having a round/hexagonal handle 52 and a blade 54 providing a cutting edge 56 and a cutting tip 58. Provided on the scalpel 50 is a blade protector 60 comprising an inner housing 62, a blade guard 64 and an outer housing 66. Although FIGS. 11-17 appear to show the protected or guarded scalpel 50 in the process of being assembled, this is for illustrative purposes only. The blade protector 60 is a unit and is attached in one motion.

The inner housing 62 is attached to the handle 52 in any suitable manner, such as by a friction fit, by the use of releasable adhesives or by a shrink fit. To this end, the inner housing 52 may be slightly elastic allowing it to be slipped over the end of the handle 52. To insure that the inner housing 62 snugly fits the scalpel handle 52, one or more flaps 68 may be stamped in a side of the housing 62 to abut the handle 52 and thereby increase friction between the housing 62 and handle 52. The inner housing 62 may be made of any suitable material, such as a medically approved polymer, and includes a partially closed forward end 70 allowing the blade 54 to pass therethrough and preventing the inner housing 52 from moving too far rearwardly on the handle 52.

The blade guard 64 slides on the outside of the inner housing 52 between a position exposing the blade 54 and a position shielding the blade 54, as may be seen by a comparison of FIGS. 17 and 19. The blade guard 64 is made of any suitable material, such as a medically approved polymer, and preferably includes a circular guard 72 and an operator 74 conveniently placed for the surgeon to push or pull in order to slide the blade guard 64 between its positions. It will, of course, be evident that the blade guard 64 may be closed and the operator 74 placed on the top of the handle 52 rather than on the bottom as shown.

The outer housing 66 is made of any suitable material, such as a medically approved polymer, and includes a closed circular member 76 secured to the inner housing 52 in a suitable manner, as by pressure welding in a spot or depression 78 rearwardly of the blade guard 64. The member 78 provides a slot 80 extending lengthwise along the handle 52 so the operator 74 is exposed through the outer housing 66. It will accordingly be seen that rearward movement of the blade guard 64 is limited by the physical connection between the inner and outer housings 62, 66.

The position of the blade guard 64 relative to the inner or outer housings 62, 66 may be controlled in any suitable manner. Because the blade guard 64 slides between the inner and outer housings, the position control may be friction between the blade guard 64 and the housings 62, 66. In other words, the blade guard 64 slides, but not readily, between the housings 62, 66. In the alternative, suitable locking means, such as a detent or bulge 82 on the blade guard 64 and one or more depressions 84 facing the detent 82. The detent 82 and depression 84, or other similar arrangement, may also provide a limit of outward movement of the blade guard 64 so it cannot accidentally be advanced off the handle 52.

Use of the scalpel 50 and blade protector 60 should now be apparent. The blade protector 60 slips over the end of the scalpel handle 52 and the blade 54 is then installed. To position the blade guard 64 in the shielding position around the blade 13, the operator 74 is advanced to a position covering the tip 58 of the blade 54, as shown in FIG. 19. To use the scalpel 50, the surgeon manipulates the operator 74 to retract the blade guard 64 thereby exposing the cutting edge 56 and tip 58 of the blade 54 as shown in FIG. 17.

Although this invention has been disclosed and described in its preferred forms with a certain degree of particularity, it is understood that the present disclosure of the preferred forms is only by way of example and that numerous changes in the combination and arrangement of parts may be made without departing from the spirit and scope of the invention as hereinafter claimed.

I claim:

1. A scalpel comprising:
   a handle having a first end and a second end providing a gripping area therebetween adapted to be gripped adjacent the palm of a surgeon's hand and a blade receiver on a terminus of the first handle end for receiving a blade having a cutting edge; and
   a blade guard assembly including:
     an elongate inner housing having a closed peripheral wall providing a passage through the inner housing, the inner housing receiving and surrounding the handle in the palm gripping area intermediate the first and second handle ends, the inner housing extending from the palm gripping area toward the blade receiver and terminating short of the blade receiver, the inner housing being removably attached to the handle independently of the blade receiver and the blade receiver being attached to the handle independently of the inner housing, an outer housing surrounding at least a portion of the inner housing, and a blade guard mounted between the inner and outer housings and slidable in relation to both the inner and outer housings between a first position exposing the blade edge and a second position shielding the blade edge.

2. The scalpel of claim 1 wherein the inner housing is frictionally fixed to the scalpel handle.

3. The scalpel of claim 2 further comprising a wedge shaped member between the inner housing and the scalpel handle for securing the inner housing to the handle.

4. The scalpel of claim 1 further comprising a flap cut from the inner housing frictionally engaging the handle for securing the inner housing to the handle.

5. The scalpel of claim 1 further comprising a friction enhancing member between the inner housing and the handle promoting a frictional fit of the inner housing to the handle.

6. The scalpel of claim 1 wherein the inner housing is secured to the handle by a releasable adhesive.

7. The scalpel of claim 1 wherein the inner housing is shrunk fit onto the handle.

8. The scalpel of claim 1 wherein the handle is flat.

9. The scalpel of claim 1 wherein the handle is round or hexagonal.

10. The scalpel of claim 1 wherein the outer housing provides a second passage therethrough closely receiving the blade guard and an elongate slot opening into the second passage, and further comprising an operator on the blade guard extending through the elongate slot.

* * * * *